United States Patent
Fulford

(10) Patent No.: US 8,048,058 B2
(45) Date of Patent: Nov. 1, 2011

(54) CATHETER TIP

(75) Inventor: Anthony Fulford, Surrey (GB)

(73) Assignee: Abbott Laboratories, Abbott Park, IL (US)

(*) Notice: Subject to any disclaimer, the term of this patent is extended or adjusted under 35 U.S.C. 154(b) by 764 days.

(21) Appl. No.: 11/241,936

(22) Filed: Oct. 4, 2005

(65) Prior Publication Data

US 2006/0030834 A1   Feb. 9, 2006

Related U.S. Application Data

(62) Division of application No. 09/969,585, filed on Oct. 4, 2001, now Pat. No. 6,964,750.

(30) Foreign Application Priority Data

Oct. 4, 2000 (GB) .................................. 0024288.3

(51) Int. Cl.
*A61M 25/00* (2006.01)

(52) U.S. Cl. ........................................ 604/523

(58) Field of Classification Search ............... 604/164, 604/407, 280, 93.01, 532, 523–529, 534, 604/282, 912, 264, 19, 164.01–164.11, 39–43
See application file for complete search history.

(56) References Cited

U.S. PATENT DOCUMENTS

| | | | |
|---|---|---|---|
| 4,420,452 A | 12/1983 | Van Dalen et al. | |
| 4,921,483 A * | 5/1990 | Wijay et al. | 604/103.1 |
| 4,961,809 A | 10/1990 | Martin | |
| 5,017,259 A | 5/1991 | Kohsai | |
| 5,205,830 A * | 4/1993 | Dassa et al. | 604/164.1 |
| 5,234,416 A * | 8/1993 | Macaulay et al. | 604/527 |
| 5,240,537 A | 8/1993 | Bodicky | |
| 5,423,773 A | 6/1995 | Jimenez | |
| 5,651,998 A | 7/1997 | Bertschi et al. | |
| 5,762,637 A | 6/1998 | Berg et al. | |
| 5,792,124 A | 8/1998 | Horrigan et al. | |
| 5,811,043 A | 9/1998 | Horrigan et al. | |
| 5,853,518 A | 12/1998 | Utas | |
| 5,860,963 A * | 1/1999 | Azam et al. | 604/528 |
| 5,919,204 A * | 7/1999 | Lukic et al. | 606/198 |
| 6,192,568 B1 | 2/2001 | Kafrawy et al. | |
| 6,322,586 B1 * | 11/2001 | Monroe et al. | 623/1.11 |

FOREIGN PATENT DOCUMENTS

EP    0 995 459 A2    4/2000

* cited by examiner

*Primary Examiner* — Matthew F DeSanto

(74) *Attorney, Agent, or Firm* — Sughrue Mion, PLLC; John Kwok

(57) ABSTRACT

A tip for attachment, in use, to the distal end of a catheter for insertion into a body lumen. The tip comprises an attachment region. The attachment region is formed from a material selected to have at least one characteristic having a first parameter of a predetermined value to enable attachment of the tip in use. There is also a second region, connected to the attachment region. The second region is formed from a material selected to have the at least one characteristic defined by a second parameter value, the second parameter value being lower than the first parameter value.

12 Claims, 2 Drawing Sheets

CATHETER TIP

Figure 1:
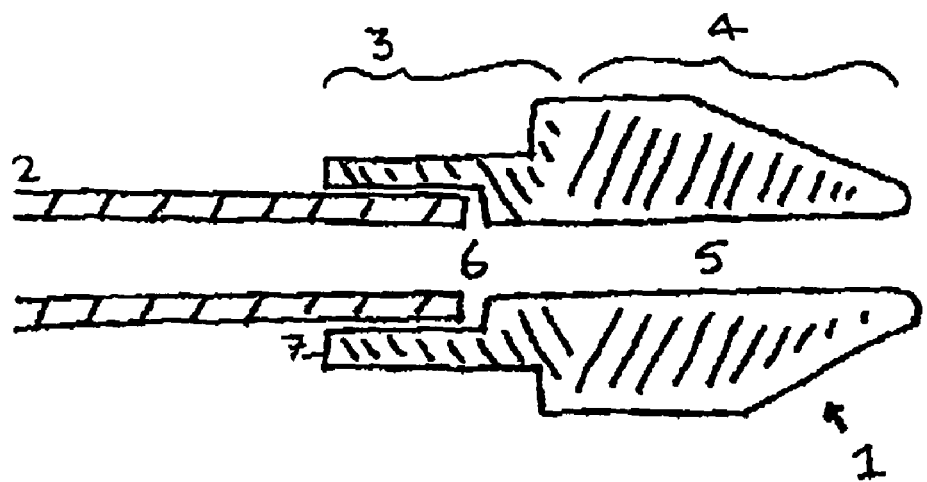
Figure 2:
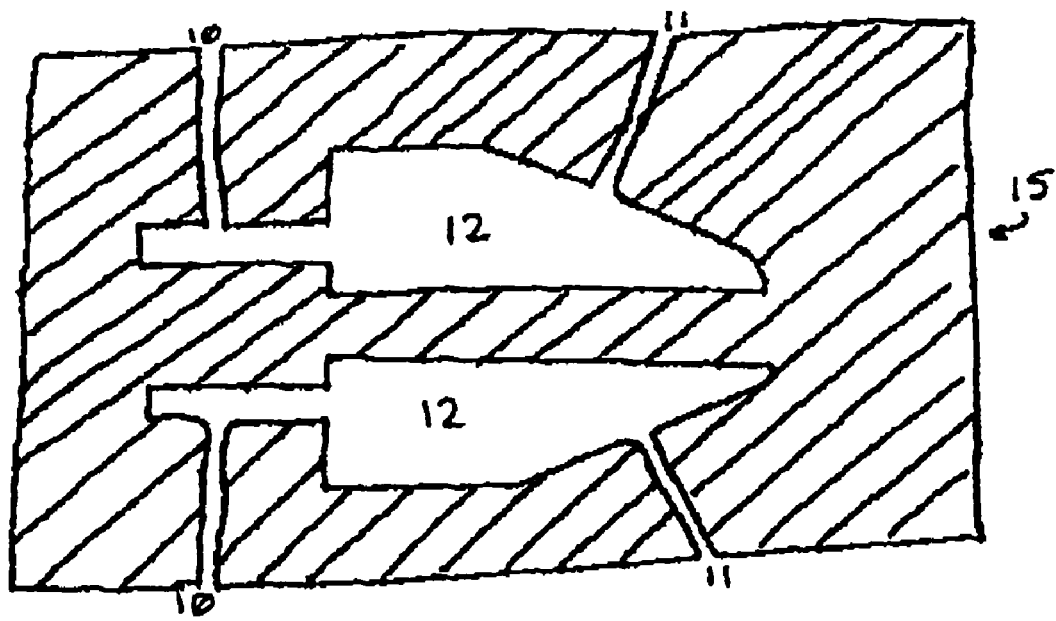

This is a divisional of application Ser. No. 09/969,585 filed Oct. 4, 2001 now U.S. Pat. No. 6,964,750. The entire disclosure of the prior application, application Ser. No. 09/969,585 is hereby incorporated by reference.

This invention relates to a catheter tip and a method of manufacturing the same.

Catheters for insertion into human and animal body lumens are well known. Such catheters are employed in a wide variety of surgical procedures and are available in a wide range of varying dimensions dependent upon the surgery in which they are to be employed and the size of lumen into which they are to be inserted.

One problem associated with such catheters is that their distal tip, the portion of the catheter which first comes into contact with a lumen, can cause severe damage to the lumen walls during insertion, particularly if formed from the same, relatively stiff, material, that it is necessary to form the main body of the catheter from.

In view of the above problem, it has been proposed to attach to the distal region of the catheter a tip formed from a material which is softer than that of the main body of the catheter, so that the softened tip will reduce the damage caused to the lumen wall during catheter insertion.

Another problem associated with catheters is that it is often difficult to locate the tip of the catheter daring insertion, making it difficult for a surgeon to determine the exact location of the catheter and to control properly insertion of the catheter, as well as the surgical procedure being performed by the catheter.

In order to overcome this problem it has been proposed to attach to the distal end of the catheter a section of radiopaque material that is readily visible using X-ray imaging or similar techniques, so that the distal tip of the catheter can be located.

Both the above two solutions have problems associated with them, however. Attachment of additional components to the tip of a catheter has to be in such a manner that safety standards can be satisfied in terms of the attachment preventing the falling-off of the additional components during use of the catheter. The safety implications of insecure fastening will be readily apparent. This results in the need for sometimes complex and intricate fastening processes chat are time consuming and costly. This problem is increased by the fact that many of the materials which are particularly soft and/or radiopaque can be extremely unreceptive to standard adhesion or bonding techniques.

In particular, one preferred approach to bonding requires the UV curing of adhesive to ensure an adequate bond. As will be appreciated, the employment of a radiopaque component means that such UV curing is difficult if not impossible, as the radiopaque component blocks transmission of the UV radiation to the curable adhesive preventing adequate curing and bonding. As another example, many softer materials are mechanically weaker, making it difficult for a strong bond to be created that will not be damaged during catheter use.

According to the present invention there is provided a tip for attachment, in use, to the distal end of a catheter for insertion into a body lumen, the tip comprising:

an attachment region, the attachment region being formed from a material selected to have at least one characteristic having a first parameter of a predetermined value to enable attachment of the tip in use; and a second region, connected to the attachment region, the second region being formed from a material selected to have the at least one characteristic defined by a second parameter value, the second parameter value being lower than the first parameter value.

The at least one characteristic may be hardness or electromagnetic radiation transmitivity, or may be a combination of both of these characteristics.

The configuration of the tip may be such that the two sections merge to form a boundary layer with one another at their join or such that there is a distinct join, between the two regions.

The regions may be formed from a plastics material such as polyether block amides (pebax), polyurethanes (for example, pellethane or tecoflex) or a synthetic rubber (for example, santoprene or neoprene). If the characteristic being determined is transmitivity then the plastics material may also comprise a radiopaque filler, such as barium sulphate. If the characteristic is hardness, then the second region plastics material may be selected to have a value in the region of 80 to 90 Shore A hardness. The first region may be formed from a similar material, but if the characteristic is transmitivity then no radiopaque filler would be present, and if the characteristic is hardness then a hardness value above that selected above is required.

The present invention also provides a method of manufacturing the above tip.

The method of manufacture may employ simultaneous infection moulding of the materials for the two regions, or may employ thermoforming of two different material sections over a mandrel to form the outside of the regions being shaped by a surrounding mould. Alternatively, the process may employ joining of two individually formed components by adhesion or ultrasonic or thermal welding.

By the provision of a tip with two regions it is possible to select characteristics for the tip which ensure adequate radiopacity or softness at the very distal end of the tip, yet still provide a tip with characteristics which are conducive either to the transmission of radiation for curing or for adequate adhesion by having adequate hardness so chat the safety requirements for bonding of the tip can be met simply and reliably.

An example of the present invention will now be described with reference to the accompanying drawings, in which:

FIG. 1 is a cross-sectional view through an example catheter tip according to the current invention; and FIGS. 2 and 3a-c illustrate alternative example manufacturing methods of the invention.

Referring to FIG. 1, a catheter tip 1, according to the invention is located, in use, on a catheter 2. The tip 1 of the present invention comprises two regions, each formed from a different material. In use, the attachment region 3 becomes the proximal portion and the second region 4 becomes the distal portion. The attachment region 3 uses a first material and the second region 4 uses a second material. These materials have a characteristic parameter which differs in each region. The characteristic may be hardness, transmitivity or surface friction. Whether the characteristic is hardness, transmitivity or surface friction, the attachment region 3 will have a higher value than the second region 4. The materials are preferably similar enough, however, so that they coalesce during the manufacturing processes that will be described below.

The second region may be formed from a plastics material such as polyether block amides (pebax), polyurethanes (for example, pellethane or tecoflex) or a synthetic rubber (for example, santoprene or neoprene). If the characteristic being determined is transmitivity then the plastics material may also comprise a radiopaque filler, such as barium sulphate. If the characteristic is hardness, then the second region plastics material may be selected to have a value in the region of 80 to 90 Shore A hardness. The first region may be formed from a similar material, but if the characteristic is transmitivity then no radiopaque filler would be present, and if the characteristic is hardness then a hardness value above that selected above is required.

The tip 1 includes a central bore 5 of internal diameter similar to that of the catheter 2, to which it is connected in use. This internal diameter increases in the attachment region 3 to provide a region 6 of increased diameter to accommodate, in use, the catheter 2. The preferred form of the exterior surface of the tip 1 is illustrated in FIG. 1 and is chamfered over the end of the second region 4, the larger diameter is then maintained into the attachment region 3 where the dimension is reduced to form an external tube 7 over the catheter 2. The end of the tip 1, defined by the second region 4, is smoothed to further aid entry and movement through a body lumen, in use.

A first example manufacturing method for forming the tip 1, Is injection moulding. The tooling 15 for such a method, to form a tip of the type described above, is illustrated in FIG. 2. The tooling 15 comprises a forming block containing a plurality of injection ports 10, 11 providing access to an internal cavity 12 which defines the shape of the tip 1 as described above. Each of the two materials forming the two regions 3, 4 are injected through their respective injection ports 10, 11 at predetermined rates to ensure that the two materials meet at the desired location in the internal cavity 12. After cooling, the formed tip 1 can then be removed from the mould.

Figure 3A:
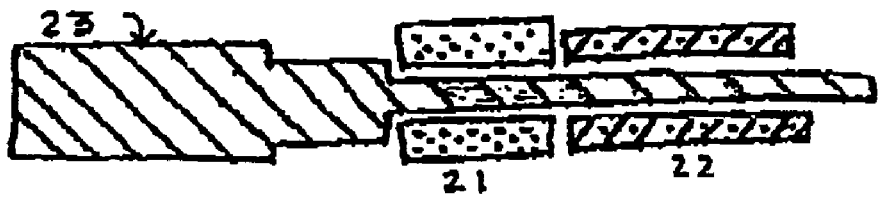
Figure 3B:
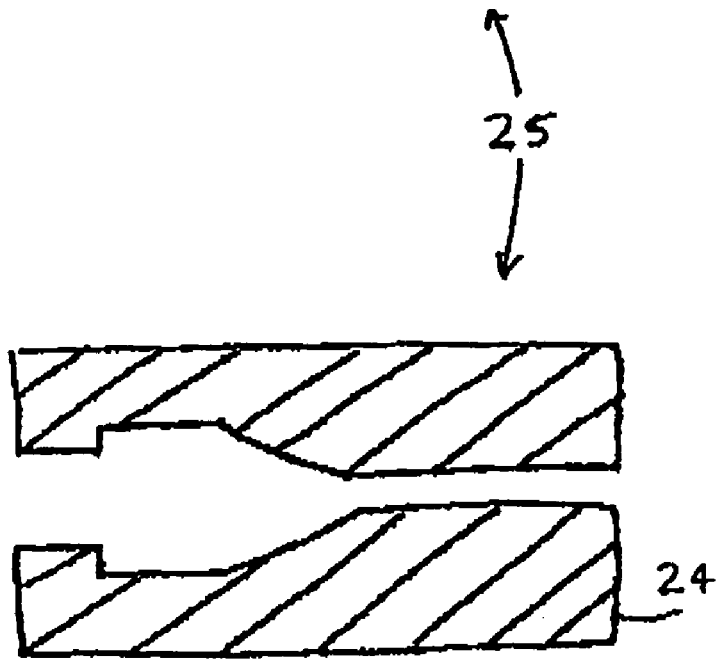
Figure 3C:
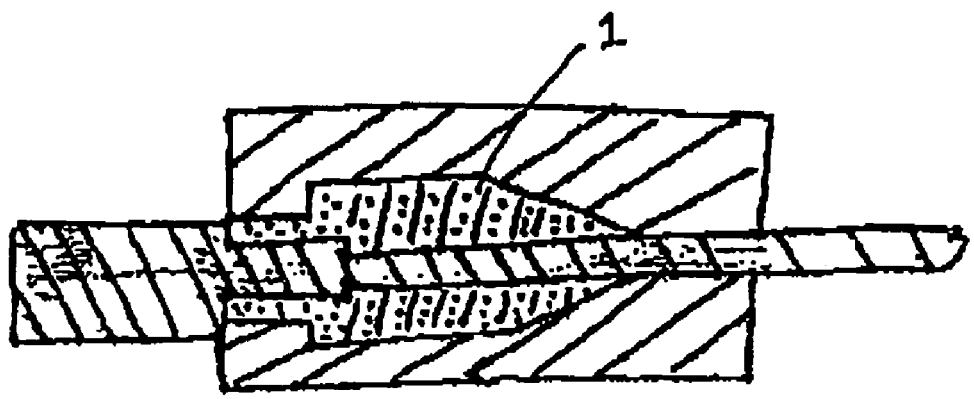

A second example manufacturing method is thermoforming or compression moulding, which is illustrated in FIGS. 3a to 3c. The tooling 25 employed in this method is in two sections, the first (FIG. 3a), an insert pin 23, defines the central bore 5 of the tip 1, complete with its step change in diameter. The second (FIG. 3b), the outer tool 24, constrains the external surface of the finished article. Blanks 21, 22 of the two materials which will form the two regions 3, 4 are positioned about the insert pin 23 which is then encompassed by the heated outer tool 24. The compressed materials melt and flow into the mould (FIG. 3c). Upon cooling the two materials form a tip 1 of the type described above with the material contact boundary in the desired location. Again, the formed tip 1 can then be removed from the mould.

The invention claimed is:

1. A tip for attachment, in use, to the distal end of a catheter for insertion into a body lumen, the tip comprising:

an attachment region having a proximal end and a distal end; and a second region having a proximal end and a distal end, the proximal end of the second region is connected to the distal end of the attachment region, wherein an internal diameter of the attachment region is larger than an internal diameter of the second region, an external diameter of the attachment region is smaller than an external diameter of a proximal part of the second region and a distal end of the second region is chamfered, the second region having a lower electromagnetic radiation transmitivity than the attachment region, and wherein the second region comprises a radiopaque filler and there is no radiopaque filler in the attachment region.

2. A tip according to claim 1, wherein the attachment region has a higher hardness than the second region.

3. A tip according to claim 1 or claim 2, wherein the second region is formed from a plastics materials selected from a polyether block amide, a polyurethane or a synthetic rubber.

4. A tip according to claim 3, wherein the second region further comprises a radiopaque filler.

5. A tip according to claim 4, wherein the second region plastics material is selected to have a value in the region of 80 to 90 Shore A hardness.

6. A tip according to claim 4, wherein the surface friction of the attachment region is higher than the surface friction of the second region.

7. A tip according to claim 3, wherein the second region plastics material is selected to have a value in the region of 80 to 90 Shore A hardness.

8. A tip according to claim 1 or claim 2, wherein the configuration of the tip is such that the two sections merge to form a boundary layer with one another at their join.

9. A tip according to claim 8, wherein the second region is formed from a plastics material such as a polyether block amide, polyurethane or a synthetic rubber.

10. A tip according to claim 9, wherein the second region plastics material is selected to have a value in the region of 80 to 90 Shore A hardness.

11. A tip according to claim 1, wherein the configuration of the tip is such that the two sections merge to form a boundary layer with one another at their join.

12. A tip according to claim 1, wherein the tip is attached to a proximal end of the catheter via an adhesive, the adhesive comprising a material that is curable using UV radiation.

* * * * *